US006562885B1

(12) United States Patent
Moorehead et al.

(10) Patent No.: US 6,562,885 B1
(45) Date of Patent: May 13, 2003

(54) COMPOSITION FOR DEACTIVATING CHEMICALLY AND BIOLOGICALLY ACTIVE AGENTS AND METHOD OF MAKING THE SAME

(75) Inventors: John S. Moorehead, Westerville, OH (US); Lynnette D. Blaney, Hilliard, OH (US); David H. Brown, Dugway, UT (US); Pierre J. Messier, Mirabel (CA); Norbert G. Laderoute, Mirabel (CA)

(73) Assignees: Battelle Memorial Institute, Columbus, OH (US); Triosyn Corporation, Mirabel (CA)

( * ) Notice: Subject to any disclaimer, the term of this patent is extended or adjusted under 35 U.S.C. 154(b) by 0 days.

(21) Appl. No.: 09/270,636

(22) Filed: Mar. 17, 1999

Related U.S. Application Data

(60) Provisional application No. 60/078,642, filed on Mar. 19, 1998.

(51) Int. Cl.[7] .................................................. C08K 3/00
(52) U.S. Cl. ......................................................... 524/80
(58) Field of Search ................................................ 524/80

(56) References Cited

U.S. PATENT DOCUMENTS

| | | | | |
|---|---|---|---|---|
| 3,923,665 A | * | 12/1975 | Lambert | 210/501 |
| 4,017,407 A | | 4/1977 | Cantor et al. | 252/106 |
| 4,094,967 A | | 6/1978 | Gilbert | 424/28 |
| 4,187,183 A | | 2/1980 | Hatch | 210/501 |
| 4,381,380 A | | 4/1983 | LeVeen et al. | 525/452 |
| 4,469,826 A | | 9/1984 | Carlick et al. | 523/339 |
| 4,483,771 A | | 11/1984 | Koch | 210/490 |
| 4,538,158 A | * | 8/1985 | Warszawski | 346/135.1 |
| 4,584,192 A | | 4/1986 | Dell et al. | 424/81 |
| 4,668,510 A | | 5/1987 | Shetty | 424/78 |
| 4,798,870 A | * | 1/1989 | Lyle | 525/327.1 |
| 5,219,580 A | | 6/1993 | Torres et al. | 424/667 |
| 5,236,703 A | | 8/1993 | Usala | 424/78.36 |
| 5,326,567 A | | 7/1994 | Capelli | 424/405 |
| 5,370,534 A | | 12/1994 | Wolf et al. | 433/80 |
| 5,431,908 A | | 7/1995 | Lund | 424/78.1 |
| 5,607,683 A | | 3/1997 | Capelli | 424/405 |
| 5,618,799 A | | 4/1997 | Inagi et al. | 514/53 |
| 5,639,452 A | | 6/1997 | Messier | 424/78.1 |
| 5,662,913 A | | 9/1997 | Capelli | 424/405 |

* cited by examiner

*Primary Examiner*—Edward J. Cain
(74) *Attorney, Agent, or Firm*—Porter, Wright, Morris & Arthur, LLP (57) ABSTRACT

A substance capable of devitalizing hazardous biological agents and deactivating hazardous chemical agents comprising an activated anion exchange resin having a particle size substantially in the range of about 0.1–300 microns, which resin particles have been iodinated by exposure to a sufficient amount of an iodine-substance absorbable by the anion exchange resin such that the resin particles absorb the iodine-substance so as to convert the resin particles into activated resin particles. The iodine-substance may be selected from the group consisting of $I_2$ (i.e., diatomic iodine), and polyiodide ions having a valence of −1. The activated resin particles may be placed into contact with the biological or chemical agent as a dry aerosol, by dust coating, or by admixing the particles with a carrier to form a coating.

49 Claims, 2 Drawing Sheets

COMPOSITION FOR DEACTIVATING CHEMICALLY AND BIOLOGICALLY ACTIVE AGENTS AND METHOD OF MAKING THE SAME

RELATED APPLICATION

This application claims the benefit of U.S. provisional patent application No. 60/078,642, filed Mar. 19, 1998.

BACKGROUND AND OBJECTS OF THE INVENTION

The present invention relates generally to a resin composition, particularly halide impregnated resin particles, and to a method of making the same. The halide impregnated resin particles may be applied to a substrate in the form of a coating or a dry aerosol. It is believed that the halide impregnated resin particles may be used to deactivate or substantially reduce the effectiveness of certain chemically and biologically active agents on contact. Thus, the present invention also relates to the use of halide impregnated particles to deactivate certain chemically and biologically active agents.

U.S. Pat. No. 5,639,452 to Messier, the content of which is incorporated herein by reference, discloses a disinfectant substance comprising an iodine impregnated ion exchange resin and a process for the preparation thereof. The Messier patent discloses that this disinfectant is a demand-type broad spectrum resin-polyiodide disinfectant useful in sterilizing fluids, and particularly a polyiodide disinfectant in which the iodine is more tenaciously associated with the resin than with previously known disinfectants, such that it leaves behind nondetectable or otherwise acceptable residual diatomic iodine in treated fluids. Thus, the patent teaches that the iodinated resin may be used to sterilize fluids such as water, air, and bodily secretions by devitalizing microorganisms such as fungi, bacteria and viruses that may be present in the fluid. It appears that this effect generally is accomplished by causing the microorganisms in the fluid to contact the resin surface and/or the resin impregnated material. U.S. Pat. No. 5,431,908 to Lund, the content of which is incorporated herein by reference, also teaches a method of preparing halide-impregnated ion exchange resins useful in purifying fluids such as water.

A devitalizing or disinfectant substance that incorporates the capabilities of a fluid disinfectant such as that described by Messier or Lund, but that is suitable for use in connection with the disinfection of nonfluid objects and deliverable in aerosolized form or incorporated into a coating would be desirable. Such a substance could be used, for example, to decontaminate a nonfluid object that is exposed to biological agents such as airborne pathogens, whether continuously or intermittently. It also could be used to provide a protective coating on nonfluid objects that are likely be exposed to biological agents such that the object would be capable of devitalizing these agents on demand, at least until the devitalizing substance present in the coating has been exhausted, without significant detriment to the object's usual utility and without application of a discrete decontamination or devitalization substance or procedure after exposure to the agent. Such a protective coating would be useful on objects that are likely to be exposed to biological agents on a more or less regular basis, for example, equipment used in medical emergency response or other health care applications or surfaces in public or institutional washrooms and shower facilities. The coating also would be useful on objects that may be exposed to such agents in the event of a catastrophe, such as a military conflict, terrorist incident or a hazardous material spill.

As used herein, "biological agent" refers to hazardous biological organisms including viruses and bacteria, whether in the form of spores or otherwise, and eukaryotic parasites such as Giardia. It also includes biologically generated toxins such as botulinum toxin. The term "devitalize" means to kill a biological agent that is an organism, or to render a biological agent inactive or substantially less effective, including, without limitation, disinfection. It is expected that the devitalizing substance will be effective against biological agents that are susceptible to oxidation by ionic halides such as polyiodide ions.

It also would be desirable to have a deactivating substance capable of reaction with and at least partial deactivation of certain chemical agents. As used herein, "chemical agent" means a hazardous chemical agent, including but not limited to chemical warfare agents such as the compounds known as GD, HD and VX, and hazardous industrial chemical agents. Also, the term "deactivate" means to render any such chemical agent inactive, ineffective, or substantially less effective for its intended purpose of causing harm to animal life or health, and particularly human life or health. As described above in connection with devitalization of biological agents, it is expected that the deactivating substance will be effective against chemical warfare agents and other chemical agents susceptible to oxidation by ionic halides such as polyiodide ions.

The above-described chemical agent deactivating substance could be used to decontaminate fluids that may contain chemical agents, to decontaminate nonfluid objects that may have such agents on their surfaces, or to provide a protective coating on nonfluid objects that are likely to be exposed to such agents. Such a protective coating may provide increased resistance to chemical agents even if it is not capable of deactivating all such possible agents. A substance capable of devitalizing biological agents and deactivating chemical agents, either independently or simultaneously depending upon the circumstances, would be particularly preferred.

In connection with the use of a devitalizing or deactivating substance to decontaminate nonfluid items, it further would be desirable to have such a substance in a dry aerosol form, such that finely divided particles of the substance may be dispersed over the item or items to be treated. Dispersal of the dry aerosol substance, for example, by fogging a room, would allow the substance to penetrate into pores, crevices or other surface irregularities that may be present in or on the item(s) to be treated. The substance also could be applied in this manner to contaminated items such as computers, electronic and electrical equipment, and other water-sensitive or water-reactive materials, that may be further harmed by contact with a liquid devitalizing or deactivating substance, and particularly a water-based substance. A suitable substance in dry aerosol form may be selected based on the electrostatic properties of a nonfluid item, such that the resin particles deposited on the surface tend to be held in engagement with the surface for a period of time. Alternatively, for nonfluid objects that are not liquid-sensitive, the dry aerosol substance may be applied to a surface that has been treated by wetting with a suitable wetting agent to cause the resin particles to remain in engagement with the surface for a desired length of time.

A dry aerosol also could be used in forming a protective coating on a substrate, for example, by "dust-coating." The devitalizing or deactivating substance in dry aerosol form could be applied to a wetted surface. The wetting agent causes the resin particles to be adhered to or within the agent, such that the particles remain in contact with the surface after drying or curing of the wetting agent. For example, the wetting agent may be a paint-type coating such as a chemical warfare agent resistant coating (CARC) or a polymeric composition.

It also would be desirable to cause the devitalizing or deactivating substance to be incorporated into a coating that may be applied to nonfluid objects to form a protective coating thereon. The resin particles may be admixed with a suitable carrier and the resultant coating applied to a surface of the object by any suitable means, for example, brushing, rolling, spraying, troweling, pouring or the like. The carrier may be a paint-type coating such as a water- or solvent-based CARC or a polymeric material. Such a coating that could be applied to objects likely to become exposed to chemically or biologically active agents, such that deactivation and devitalization of these agents could begin on contact with the object and the object could be maintained essentially free from contamination by such agents during the effective life of the halide-resin composition.

In addition, it would be advantageous to have a halide-resin composition that has characteristics superior to known iodide-resin disinfectants. For example, a halide-resin having an increased surface area to provide more rapid deactivation of biologically active agents, and particularly a finely divided resin suitable for dispersion as a dry aerosol, would offer advantages. A halide-resin composition capable of deactivating, or at least partially deactivating, chemically active agents such as nerve gases in addition to biologically active agents, also would offer particular advantages.

These and other objects of the present invention will be apparent from the specification that follows and the appended claims.

SUMMARY OF THE INVENTION

In accordance with these objectives, a resin composition capable of devitalizing biological agents and deactivating chemical agents may comprise halide-resin particles comprising polyhalide ions having a valence of −1 absorbed or impregnated into resin particles having a particle size substantially in the range of about 0.1–15 microns. The halide-resin may be characterized in that an activated halogenated resin is divided into particles substantially in the range of about 0.1–15 microns before exposure to a sufficient amount of a halogen-substance absorbable by the activated resin to form converted resin particles having a greater proportion of available ionic halogen, with the halogen-substance being selected from the group consisting of $I_2$, $Br_2$, and polyiodide ions having a valence of −1. The halide-resin particles may, for example, have a particle size substantially in the range of about 0.1–3 microns, 3–5 microns, 3–15 microns, or 5–15 microns.

The resin composition also may comprise halide-resin particles comprising polyhalide ions having a valence of −1 absorbed or impregnated into resin particles and characterized in that an activated halogenated resin is divided into particles substantially in the range of about 15–300 microns before exposure to a sufficient amount of a halogen-substance absorbable by the activated resin to form converted resin particles having a greater proportion of available ionic halogen. The halogen-substance is selected from the group consisting of $I_2$, $Br_2$, and polyiodide ions having a valence of −1.

As used herein, the terms "polyhalide," "polyhalide ions," and the like refer to or characterize a substance or a complex that has three or more halogen atoms and a valence of −1, and which may be formed if a molecular halogen (e.g., bromine as $Br_2$) combines with a monovalent trihalide ion (e.g., triiodide ion) or pentahalide ion (e.g., pentaiodide ion). Iodine and chlorine also may be used as a source of molecular halogen. Similarly, the terms "polyiodide," "polyiodide ions," and the like refer to or characterize a substance or a complex that has three or more iodine atoms and that may be formed if molecular iodine combines with the monovalent triiodide ion. The terms "triiodide, "triiodide ion," and the like refer to or characterize a substance or a complex that contains three iodine atoms and has a valence of −1. The triiodide ion herein therefore is a complex ion which may be considered as comprising molecular iodine (i.e., iodine as $I_2$) and an iodine ion (i.e., $I^-$).

The above-described converted resin particles may be capable of being dispersed in dry aerosol form. The converted resin may be capable of reducing the activities of target chemical agents, biological agents, and biologically generated toxins. A single resin may be capable of reducing the activities of both chemical and biological agents. The devitalizing and deactivating resin may be a demand-type devitalizer and deactivator, i.e., a substance from which halide ions are released almost entirely on a demand-action basis upon contact with a target agent but that does not otherwise release substantial amounts of the devitalizing and deactivating substance into the environment. Such a demand-type substance essentially would be capable of devitalizing and deactivating target agents on demand, at least until the halide-resin has been exhausted.

The invention includes a method of making a resin composition, comprising the steps of:
providing an activated halide-resin;
forming the activated resin into particles;
selecting resin particles substantially in the range of about 0.1–300 microns; and
forming converted resin particles having a greater proportion of available ionic halogen.

The step of selecting resin particles may, for example, include selecting particles substantially in the range of about 0.1–3 microns, 3–5 microns, 3–15 microns, 5–15 microns, or 15–300 microns. It also may include selecting an anionic triiodide resin or a divinyl styrene triiodide resin.

Converted resin particles may be formed by exposing the resin particles to a sufficient amount of a halogen-substance to form converted resin particles, the halogen-substance being selected from the group consisting of $I_2$, $Br_2$, and polyhalide ions having a valence of −1. Absorption of at least a portion of the halogen-substance may be effected at elevated temperatures, i.e., temperatures higher than 100° C. and up to 210° C., and elevated pressures, i.e., pressures greater than atmospheric pressure and up to 100 psig.

The present invention also provides a demand chemical-agent deactivator, comprising halide-resin particles comprising polyhalide ions having a valence of −1 absorbed or impregnated into resin particles having a particle size substantially in the range of about 0.1–300 microns. The resin particles of the deactivator may, for example, have a particle size substantially in the range of about 0.1–3 microns, 3–5 microns, 3–15 microns, 5–15 microns, or 15–300 microns. The resin may be an anionic resin, a divinyl styrene resin, or a quaternary ammonium resin. The halide-resin particles may be polyiodide-resin particles, which may be predominantly triiodide-resin particles. The deactivator may be capable of being dispersed in dry aerosol form.

The invention also provides a method of deactivating target agents, comprising the steps of:

providing an activated halide-resin;

forming the activated resin into particles;

selecting resin particles substantially in the range of about 0.1–300 microns;

exposing the resin particles to a sufficient amount of a halogen-substance absorbable by the activated resin to form converted resin particles having a greater proportion of available ionic halogen, the halogen-substance being selected from the group consisting of $I_2$, $Br_2$, and polyhalide ions having a valence of −1; and placing the converted resin particles in contact with a target agent selected from chemical agents, biological agents, and biologically generated toxins. Absorption of at least a portion of the halogen-substance may be effected at elevated temperatures and elevated pressures as described above.

The step of selecting resin particles may include selecting particles substantially in the range of about 0.1–3 microns, 2–3 microns, 3–5 microns, 3–15 microns, 5–15 microns, 15–50 microns, or 15–300 microns. The step of providing an activated halide-resin may include selecting an activated halide-resin having a electrostatic charge that assists in maintaining converted resin particles in engagement with a substrate.

In accordance with the objective of using the converted resin for decontamination of nonfluid objects, the step of placing converted resin particles in contact with a target agent may include dispersing the converted resin particles as a dry aerosol, imparting an electrostatic charge to the converted resin particles to assist in maintaining them in engagement with a surface, or providing a surface that is electrostatically charged to maintain the converted particles in engagement with the surface. The step of placing converted resin particles in contact with a target agent also may include providing a wetted surface and causing a portion of the converted particles to be deposited on the wetted surface. The step of providing a wetted surface may include selecting a surface wetting agent capable of retaining converted resin particles deposited on a surface wetted with the wetting agent.

In accordance with the objective of using the converted resin in a protective coating, the step of placing converted resin particles in contact with target agent may include the steps of:

providing a carrier capable of holding the converted resin particles in suspension;

suspending the converted particles in the carrier; and applying the suspension to a surface.

The step of providing a carrier may include selecting a carrier that does not materially interfere with the ion exchange capability of the converted resin or that comprises a chemical agent resistant coating. This step also may include providing a predetermined volume of pigment particles and the step of suspending the converted resin particles in the carrier may include suspending a volume of converted resin particles approximately equal to the volume of pigment particles.

The invention also includes an aerosol capable of reducing the effectiveness of target agents, such as chemical agents, biological agents, and/or biologically generated toxins. The aerosol substance comprises halide-resin particles comprising polyhalide ions having a valence of −1 absorbed or impregnated into resin particles and characterized in that an activated halogenated resin is divided into particles substantially in the range of about 0.1–300 microns before exposure to a sufficient amount of a halogen-substance absorbable by the activated resin to form converted resin particles having a greater proportion of available ionic halogen, with the halogen-substance selected from the group consisting of $I_2$, $Br_2$, and polyiodide ions having a valence of −1. The halide-resin particles may be further characterized in that an activated halogenated resin is divided into particles substantially in the range of about 0.1–3 microns, 3–15 microns, or 15–300 microns before exposure to the halogen-substance.

The converted resin particles are capable of being dispersed as a dry aerosol. The particles may be electrostatically charged to assist in maintaining the particles in engagement with a substrate, with the particles being electrostatically charged prior to being dispersed. Preferably, the electrostatic charge difference between the particles and the substrate will be sufficient to permit the particles to adhere to vertical surfaces and the like. The converted resin particles may, for example, be passed through a nozzle so that they engage a static charge inducing substance in the nozzle.

The invention also includes a coating capable of reducing the effectiveness of target agents. The coating comprises halide-resin particles comprising polyhalide ions having a valence of −1 absorbed or impregnated into resin particles and characterized in that an activated halogenated resin is divided into particles substantially in the range of about 0.1–300 microns before exposure to a sufficient amount of a halogen-substance absorbable by the activated resin to form converted resin particles having a greater proportion of available ionic halogen, with the halogen-substance being selected from the group consisting of $I_2$, $Br_2$, and polyiodide ions having a valence of −1; and a carrier holding the converted resin particles in suspension. The converted resin is capable of reducing the effectiveness of targets including chemical agents, biological agents, and/or biologically generated toxins.

The halide-resin particles may be further characterized in that an activated halogenated resin is divided into particles substantially in the range of about 0.1–3 microns, 3–15 microns, or 15–300 microns before exposure to the halogen-substance. The converted resin particles are at least 20 percent larger than the particles of any pigment present in the carrier.

The carrier preferably does not materially interfere with the ion exchange capability of the converted resin. The carrier may be a chemical warfare agent resistant coating, a hazardous industrial chemical resistant coating, a coating that is selectively permeable to specific fluids, or a latex. The carrier may include a predetermined volume of pigment particles and the volume of converted resin particles suspended in the carrier may be approximately equal to the volume of pigment particles. The combined volumes of the pigment particles and the converted resin particles may approach the critical pigment volume of the carrier or be at least about 90% of the critical pigment volume of the carrier.

The invention further includes a method of making a protective coating, comprising the steps of:

providing an activated halide-resin;

forming the activated resin into particles;

selecting resin particles substantially in the range of about 0.1–300 microns;

exposing the resin particles to a sufficient amount of a halogen-substance absorbable by the activated resin to form converted resin particles having a greater proportion of available ionic halogen, the halogen-substance being selected from the group consisting of $I_2$, $Br_2$, and polyhalide ions having a valence of −1;

providing a carrier capable of holding converted resin particles in suspension; and suspending the activated particles in the carrier.

Absorption of at least a portion of the halogen-substance may be effected at elevated temperatures and elevated pressures.

The step of selecting resin particles may include selecting particles substantially in the range of about 0.1–3 microns, 3–15 microns, or 15–300 microns. This step also may include selecting particles that are at least twenty percent larger than the particles of any pigment present in the carrier.

The step of providing a carrier may include selecting a carrier that comprises a chemical agent resistant coating. The step of providing a carrier may include providing a predetermined volume of pigment particles and the step of suspending the converted resin particles in the carrier may include suspending a volume of converted resin particles approximately equal to the predetermined volume of pigment particles.

The method includes the step of selecting the predetermined volume of the pigment particles and a volume of converted resin particles such that the combined volumes approach the critical pigment volume of the carrier, or are at least about 90% of the critical pigment volume of the carrier. The method also may include the step of selecting a volume of the pigment particles and a volume of converted resin particles such that the combined volumes do not exceed the capacity of the binding resin in the coating to maintain the physical integrity of the cured coating with the extended pigment volume or the step of selecting a pigment particle density greater than the density of the resin particles.

The method may further include the step of selecting environmental conditions for drying the coating, the environmental conditions comprising a combination of cure temperature and relative humidity that yield a drying time sufficient to allow the resin particles to preferentially migrate to the coating surface. Preferably, the cure temperature is in the range of about 60° to 90° F. and the relative humidity is in the range of about 70 to 90 percent.

The step of providing a carrier may include selecting a carrier that does not materially interfere with the ion exchange capability of the converted resin. If the carrier interferes with the activity of the resin particles, the method may further include the steps of applying the coating to a substrate and treating the coating to improve the effectiveness of the resin particles. The treating step may include mechanically abrading or partially dissolving the coating surface to expose the resin particles such that their activity against target agents is unimpeded. The treating step also may include applying a fixative layer to the coating surface and adhering a layer of resin particles to the fixative layer.

These and further objects of the invention will become apparent from the following detailed description.

DETAILED DESCRIPTION OF THE PREFERRED EMBODIMENT(S)

STARTING MATERIAL

The composition of the present invention may be prepared starting with a commercially available polyhalide-resin having a sufficient quantity of available (i.e., loosely bound) ionic halogen. The starting resin comprises polyhalide ions having a valence of −1 absorbed or impregnated into the resin. The starting resin may in particular be a polyiodide-resin, most preferably, triiodide-resin (i.e., resin having triiodide ions of formula $I_3^-$ absorbed thereon). Preferred starting resins include Triosyn® iodinated divinyl styrene-based resins, available from Hydro Biotech, Québec, Canada.

The starting polyhalide-resin may take any commercially available form, for example, finely divided fragments or granules, beads, plates or sheets. Preferably, the starting resin is consistently-sized beads. Acceptable results have been obtained using Triosyn® resin beads of approximately 1.5 mm diameter.

Generally, the starting polyhalide-resin is prepared from a porous strong base anion exchange resin in a salt form. The anion exchange resin is exposed to a sufficient amount of a halogen-substance (such as those described herein) absorbable by the anion exchange resin so as to convert the anion exchange resin into an "activated" resin. For example, a suitable triiodide starting resin may be prepared from a divinyl styrene ion exchange resin as described in U.S. Pat. No. 5,369,452 to Messier. It is believed that halogenated resins prepared using a quaternary ammonium ion exchange resin as described in U.S. Pat. No. 5,431,908 to Lund and other suitable anion exchange resins also may be useful in the practice of this invention.

Generally, the ion exchange resin used in preparing the starting resin must have physical and chemical properties, such as plasticity and stability, compatible with the particular activation process to be used and will be capable of binding to the ionic side of halogen complexes but not to the molecular side of these complexes. Ion exchange resins useful in the practice of the invention typically will be available in the chloride or sulfate form, in which case the ion exchange resin preferably is reacted to obtain the iodide ($I^-$) or bromide ($Br^-$) form of the resin before activation.

Halogen-substances useful in preparing the activated resin typically will be selected from the group consisting of diatomic iodine, diatomic bromine, and polyiodide ions having a valence of −1. The term "halogen-substance" includes a polyhalide salt carrier solution circulated in contact with an elemental halide as described by Lund. For at least some ion exchange resins, the absorption of at least a portion of the halogen-substance preferably is effected at elevated temperature and at elevated pressure.

GRINDING/MILLING

The activated resin is processed to achieve resin particles of the desired particle size, preferably substantially in but not limited to the range of about 0.1–300 microns, including, by way of example, ranges of about 0.1–3 microns, 3–15 microns, and 15–300 microns. Small particles are desirable not only because they provide a high surface area for interaction with chemical and/or biological agents, but also because they ease dispersal of dry aerosol resin forms and yield a more durable coating when applied as an admixture.

Particles in the range of about 3–5 microns (mass median diameter) are preferred for dry aerosol applications, although other particle sizes may be used in appropriate cases. Particles in the range of about 5–15 microns (mass median diameter) are preferred for coating applications, although somewhat larger or smaller particles also may be used depending on the method of application and environmental conditions. Ultimately, the selection of particle size is based on consideration of the chemical and/or biological agent size and the environment in which the application is used.

As explained further below, a narrow distribution of particle size contributes to the effectiveness of the resin particles in devitalizing and deactivating biological and chemical agents. Preferably, the size distribution is within 3 standard deviations (3σ).

Resin particles of the desired size may be produced by processing the activated resin (preferably starting with the bead form) using conventional noncryogenic grinding and/or milling devices. Satisfactory results have been obtained using an impact grinder with a stainless steel wheel in combination with a jet mill. Consistent feed and extraction rates are helpful. The resultant powder is sieved to remove oversized particles, which may be reprocessed. Undersized particles generally are discharged during processing. Scale-up was achieved using a cryogenic grinding process.

Commercially available ion exchange resins (such as those used to produce the activated resin described herein) are extremely difficult to process into particles within the desired 0.1–300 micron range before activation of the resin and loss rates are expected to be unacceptable even when it is possible to do this. Halogenation of the resin alters its crystal structure, and thus its fracture properties, making grinding and milling somewhat easier. A resin having an iodine content of at least about 30% is preferred to achieve reasonably grindable resin. Resins having an even higher iodine content are likely to exhibit improved grindability.

The direct halogenation of commercially available ion exchange resin particles of the desired size is disfavored for other reasons. It is believed that processing of such ion exchange resins (e.g., drying of divinyl styrene ion exchange resins) to improve grindability using conventional methods may make it more difficult to halogenate the ion exchange resin particles or affect the ability of the ion exchange resin particles to absorb the halogen-substance in amounts sufficient to yield an effective deactivating and devitalizing substance. For example, directly halogenated ion exchange resin particles are expected to have less halogen in the particle core, and thus, a shorter effective life, than halide-resin particles of the present invention. It also is believed that resins prepared by direct halogenation of commercial ion exchange resin particles will be more susceptible to agglomeration than halide-resins of the present invention. Thus, it is preferred that the resin initially be activated before grinding and/or milling rather than grinding or milling the strong base anion exchange resin before activation.

CONVERSION (REACTIVATION)

Grinding and/or milling of the activated resin into resin particles in the range of about 0.1–300 microns results in some particles predominantly having absorbed halogen ions in less available forms than the preferred trihalide ion. For optimum performance, it therefore is necessary to reactivate the activated resin particles such that they possess a greater proportion of available ionic halogen than that present in the activated resin particles. This reactivation of activated resin particles is referred to as conversion. Conversion is accomplished by contacting finely divided particles of an activated halide-resin with a sufficient amount of a halogen-substance absorbable by the activated resin to form converted resin particles having a greater proportion of available ionic halogen. This causes an increase in the proportion of available ionic halogen in the halide-resin particles.

Before beginning conversion, the activated resin may be treated to remove components that may interfere with absorption of the halide into the resin. For example, the resin may be washed with water to remove undesirable elements such as material in ionic form. The wash water and other water used in making the converted resin should be free of interfering elements such as interfering ions. Distilled or deionized water is preferably used, with water obtained using double reverse osmosis being particularly preferred. The activated resin also may be subjected to an alcohol wash to dissolve undesirable organic material that may be adhering to the resin.

Conversion may be accomplished, for example, by exposing the activated resin particles to a sufficient amount of a halogen-substance absorbable by the activated resin to form converted resin particles. The halogen-substance used in accomplishing this conversion may be any material or substance capable of donating a halogen-member absorbable by the activated resin to form converted resin particles having a greater proportion of available ionic halogen, as long as the denotable halogen-member thereof is diatomic iodine, diatomic bromine, or a polyiodide ion having a valence of −1. Examples of such materials include compositions comprising iodine ($I_2$), bromine ($Br_2$) and alkali metal or other halides, such as potassium iodide, sodium iodide and ammonium iodide in association with water. For example, iodine may be combined with the preferred alkali metal halide, potassium iodide and a minor amount of water, i.e., an amount of water sufficient to avoid $I_2$ crystallization. The composition will contain monovalent iodine ion that will combine with diatomic iodine ($I_2$) to form a polyiodide ion. As used herein, "halogen-substance" includes a polyhalide salt carrier solution circulated in contact with an elemental halide.

Unless preparation of a mixed halide resin is desired, the halogen-substance selected should comprise the same halide present in the activated resin. For example, the halogen-substance used for conversion of a Triosyn® activated resin would comprise an iodine-substance, i.e., a substance selected from the group comprising crystalline of iodine ($I_2$) and polyiodide ions having a valence of −1.

The molar ratio of halogen ion to diatomic halogen will determine the nature of the polyhalide ion present, i.e., trihalide ion and mixtures of trihalide ion and higher polyhalide ions, e.g., pentahalide ion. For example, use of about 1 mole of iodine ion per mole of diatomic iodine favors the formation of triiodide ion while use of a stoichiometric excess of diatomic iodine favors the formation of higher polyiodides. Preferably, the molar ratio of halogen ion to diatomic halogen will favor association of the converted resin predominantly with trihalide ion, and particularly triiodide ion. Thus, use of stoichiometric amounts of the halogen (e.g., iodine) ion and halogen (e.g., iodine) molecule (i.e., one mole of $I_2$ per mole of $I^-$) is preferred.

The total amount of halogen to be contacted with the activated resin, residence times, reaction conditions and the like will depend upon such factors as the nature of the polyhalide it is desired to introduce into the structure of the activated resin, the nature of the activated resin, the intended use of the converted resin, and the desire to minimize the amount of unabsorbed halogen that must be washed from the converted resin particles. For use of the resin in coatings, the ratio of iodine to resin in the converted resin composition preferably will be in the range of about 50%. Higher iodine to resin ratios are thought to yield superior results in decontamination applications (for example, dispersal of the resin as a dry aerosol).

In accordance with the present invention, conversion of the activated resin, and particularly Triosyn® resin, may be effected at elevated temperature greater than 100° C., for example in the range of 105° C. to 150° C. (e.g., 110°–115° C. to 150° C.); the upper limit of the temperature used will depend, among other things, on the characteristics of the resin being used. The elevated pressure is any pressure above ambient pressure (e.g., a pressure greater than atmospheric or barometric pressure, i.e., 0 psig). The pressure may, for example, be 1 psig or higher, e.g., in the range from 5 to 50 psig; the upper limit of the pressure used will depend, among other things, on the characteristics of the resin being used.

The conversion at elevated conditions may be effected in a reactor that is pressure sealable during conversion but that may be opened for recovery of the resin product after a predetermined reaction time. The process may thus be a batch process wherein conversion at elevated temperature and pressure is effected once the reactor is sealed. The reactor may be sized and the amount of reactants determined so as to provide a void space in the reactor during reaction such that contact takes place under an essentially halogen-rich atmosphere.

The pressure in the closed vessel or reactor used to convert the resin to a polyhalide may be a function of the temperature, such that the pressure may vary with the temperature approximately in accordance with the ideal gas equation PV=nRT, wherein V=the constant (free) volume of the reactor, n=moles of material in the reactor, R is the universal gas constant, T is the temperature and P is the pressure. In a closed vessel, the temperature of the system may therefore be used as a means of achieving or controlling the desired pressure in the vessel depending upon the makeup of the halogen-substance in the reactor. Thus, a reaction mix disposed in a pressure sealed reactor may, for example, be subjected to a temperature of 105° C. and a pressure of 200 mm Hg.

Alternatively, a relatively inert gas may be injected into a sealed reactor to induce and/or augment the pressure in the reactor. Iodine, an inert (noble) gas, air, carbon dioxide, nitrogen or the like may be used as a pressuring gas, provided the chosen gas does not unduly interfere with the production of a suitable halogenated resin. If pressure is to be induced by steam, steps should be taken to isolate the reaction mix from excess water. The inert gas preferably is used to augment the pressure resulting from the use of elevated temperatures to effect conversion.

The residence or contact time at the elevated conditions may vary depending upon the starting materials, contact conditions, amount of tenaciously held halogen it is desired to be absorbed by the activated resin, and other process factors. The contact time may thus take on any value; however, it is expected generally that the contact time under the conditions used will be sufficient to maximize the amount of tenaciously held halogen absorbed from the material containing the absorbable halogen-substance. The residence time may for example be as little as 5 to 15 minutes (in the case where a preimpregnation step is used, as described below) or several hours or more (e.g., up to 8 or 9 hours or more).

Contact at high temperature/pressure may be preceded by an initial impregnation or absorption step (first stage), during which the reaction mixture may be shaken or agitated if desired. The residence time of such a first stage may be only a few minutes (e.g., for from 1 to 10 minutes or more) or for up to 24 hours or more (e.g., for from one hour or more, or from three to twenty-four hours). If the residence time is sufficiently short, such that the time corresponds roughly to the time necessary to mix the reactants together, the conversion may be considered to be essentially carried out in a single stage at elevated conditions. The residence time of the first stage depends in part on the end product resin desired. For example, a water containing sludge of triiodide ions can be contacted with the activated resin at ambient (i.e., room) temperature and pressure conditions to obtain an intermediate iodide-resin conversion product including residual iodine-substance. This step is preferably carried out in a batch reactor; the obtained intermediate composition comprising an intermediate iodide-resin may then be subjected to the higher temperature and pressure in accordance with the present invention in batch fashion as well. Such a first stage may be used to initiate buildup of iodine within the resin matrix.

The elevated temperature/pressure contact conditions may be chosen to maximize the halogen content of the obtained halide-resin. For Triosyn® resins in which the halogen-substance used during conversion includes crystalline of iodine, exposure of the activated resin to the halogen-substance at a temperature and pressure at or about the triple point of crystalline of iodine is believed to promote absorption of the maximum amount of available iodine.

It is believed that mixed polyhalide-resins also may be useful in the practice of the invention. Conversion of mixed polyhalide-resins may be carried out in two steps. In the first step, the activated resin may be exposed to a halogen-substance containing a first elemental halogen (e.g., diatomic iodine) in a quantity sufficient to form some converted polyiodide-resin and unconverted resin. In the second step, the resin mixture is exposed to a halogen-substance containing a second elemental halogen (e.g., diatomic bromine) in a quantity sufficient to convert the unconverted resin to polybromide-resin.

The converted halide-resin may be treated prior to use to remove any water-elutable iodine, such as, for example, potassium iodide, from the surface of the halide-resin so that on drying of the resin, no crystals of halogen compounds will form on the surface of the halide-resin. The treatment (e.g., washing) may be continued until no detectable iodine (e.g., a total iodine content of less than 0.1 parts per million) or other halogen is found in the wash water. Any suitable iodine test procedure may be used for iodine detection purposes, if desired.

The present invention further comprises a process for preparing converted resin particles from an activated resin, the activated resin being an iodinated strong base anion exchange resin, (i.e., resin having polyiodide ions and with a valence of −1 absorbed or impregnated into the resin as herein described). The process includes the step of forming the activated resin into particles of a desired size, for example, by grinding and/or milling. The process further includes a conversion step, the conversion step comprising contacting the activated resin particles with a sufficient amount of an halogen-substance absorbable by the activated resin to form converted resin particles having a greater proportion of available ionic halogen. The halogen-substance is selected from the group comprising $I_2$ (i.e., diatomic iodine), $Br_2$ (i.e., diatomic bromine), and polyiodide ions having a valence of −1.

The conversion step may be characterized in that absorption of at least a portion of the halogen-substance is effected at elevated temperature and at elevated pressure, the elevated temperature being 100° C. or higher (e.g., a temperature higher than 100° C.) and the elevated pressure being greater than atmospheric pressure. The conversion may essentially or at least partially be effected at an elevated temperature and elevated pressure. The conversion thus may be effected in one, two or more stages. For example, the elevated pressure/temperature conditions may be divided between two different pairs of elevated pressure/temperature conditions, e.g., an initial pressure of 15 psig and a temperature of 121° C. and a subsequent pressure of 5 psig and a temperature of 115° C.

If the conversion is to be carried out in two stages, it may, for example, comprise a first stage followed by a second stage, and more particularly, a first stage effected at low temperature and pressure conditions (e.g., at ambient temperature and ambient pressure conditions) and a second stage may be effected at elevated conditions. For example, the first stage may be effected at a temperature of not more than 95° C.; e.g., 15° to 60° C.; e.g., ambient temperature or room temperature such as a temperature of from about 15° C. to about 40° C., e.g., 20° to 30° C., and a pressure of from 0 (zero) to less than 2 psig; the pressure may in particular be essentially ambient pressure (i.e., a pressure of less than I psig to 0 psig). The second stage may be effected at a temperature of 102° C. or higher; e.g., 105° C. or higher; e.g., 110° C. or higher; e.g., 115° C. or higher; e.g., up to 150° C. to 210° C.; e.g., 115° C. to 135° C., and a pressure of 2 psig or greater; e.g., 5 psig or greater; e.g., 15 psig to 35 psig; e.g., up to 100 psig.

In a two-stage conversion process, for example, the first stage may comprise contacting an activated triiodide resin with an iodine-substance at a temperature of 100° C. or lower so as to obtain an intermediate composition, the intermediate composition comprising residual absorbable iodine-substance and an intermediate iodinated resin, (i.e., an activated resin comprising absorbed polyiodide ions having a valence of −1), and the second stage may comprise subjecting the intermediate composition to elevated temperature and elevated pressure, the elevated temperature being 100° C. or higher (e.g., a temperature higher than 100° C.) and the elevated pressure being greater than atmospheric pressure.

USE OF CONVERTED RESIN

1. AEROSOL

The converted resin particles may be placed in contact with a target biological or chemical agent by dispersing the resin particles as a dry aerosol such that finely divided particles of the substance are dispersed over the item or items to be treated. Particles in the range of about 3–5 microns (mass median diameter) are preferred for many dry aerosol applications.

The resin particles may be dispersed using a conventional aerosolizer with a Venturi stream. A portable aerosolizer may be used for decontamination in the field. The particles preferably are deagglomerated, for example, in an attritter, immediately before being dispersed.

A. DECONTAMINATION

The aerosolized resin particles may effectively be used alone in certain applications, such as the decontamination of items with rough or irregular surfaces as well as computers, electronic and electrical equipment, and other water-sensitive or water-reactive materials or equipment. Dispersal of the dry aerosol substance, for example, by fogging of a room or other area, is thought to allow the substance to penetrate into pores, crevices or other surface irregularities that may be present in or on the item(s) to be treated. This also would allow the substance to be applied to items, such as computers, electronic and electrical equipment, and other water-sensitive or water-reactive materials, that may be further harmed by contact with a liquid devitalizing or deactivating substance, and particularly a water-based substance.

Preferably, the size of the aerosolized particles is approximately equal to the size of the particles or droplets of the target agent against which the resin particles are expected to be used. Aerosolized resin particles in the about 3–5 micron size range are thought to be capable of penetrating equipment and structures to about the same degree as target agents of this size range, thus enabling the converted resin particles to devitalize and deactivate the target agents. A narrow particle size distribution is preferred so that the behavior of the resin particles, whether airborne or in contact with surfaces, more nearly approximates that of the target agents. In addition, use of particles in this size range minimizes the likelihood that contaminants will be able to fit between the particles that engage a surface.

A quantity of resin particles sufficient to evenly and thoroughly cover the substrate of interest is necessary to achieve effective decontamination. If the resin particles are applied too thinly or unevenly, decontamination is likely to be less effective because the resin particles will not have been in contact with all areas of the substrate, allowing target agents present in those areas to remain in their active forms.

The method of placing the devitalizing or deactivating substance in dry aerosol form in contact with a substrate may depend on the substrate and the agent to be treated. The aerosolized particles are likely to adhere effectively to damp surfaces (such as those that recently have been in contact with a liquid or misted target agent) and horizontal surfaces in calm air without additional steps. When these conditions are not present, selection of the converted resin may be based on the electrostatic properties of the nonfluid objects to be contacted, such that the resin particles deposited on the surface tend to be held in engagement with the surface for a period of time. This resin particles also may be caused to contact a static charge-inducing material, such as rubber in the barrel of the aerosolizer nozzle, before the particles enter the Venturi stream to impart an electrostatic charge to the particles. Alternatively, the substrate may be treated to impart an electrostatic charge that tends to attract the resin particles. A sufficient difference between the electrostatic properties of the resin particles and the substrate generally is necessary to retain the substance in contact with nonhorizontal surfaces for a desired time.

Dry aerosol application for decontamination also could include providing a treated surface capable of retaining aerosolized resin particles in engagement with the substrate. For example, the surface of the substrate may be treated such that the resin particles deposited on the treated surface tend to be held in engagement with the surface for a period of time. For nonfluid objects that are not liquid-sensitive, aerosol application may include providing a wetted surface and causing a portion of the aerosolized particles to be deposited on the wetted substrate. Any suitable wetting agent (i.e., a wetting agent compatible with the surface and that does not interfere to any material extent with the ion exchange capability of the converted resin) may be used. Thus, the method also may include selecting a suitable wetting agent to be applied to the substrate.

B. DUST-TYPE COATING

In addition to use in decontamination, the devitalizing or deactivating substance in dry aerosol form also may be used in forming a protective coating by dispersing or "dusting" the particles onto a wetted surface. Placement of the devitalizing or deactivating substance in contact with a chemical or biological agent therefore may include providing a treated surface capable of retaining aerosolized resin particles in engagement with the substrate for a period of time. The method also may include the step of selecting a wetting agent to be applied to the surface. Any suitable wetting agent (i.e., a wetting agent compatible with the surface and that does not interfere to any material extent with the ion exchange capability of the converted resin) may be used.

The wetting agent preferably comprises a composition that causes the resin particles to be adhered to or within the composition such that the particles remain in contact with the surface after drying or curing of the wetting agent. The wetting agent therefore may be a paint-type coating, preferably, a chemical warfare agent resistant coating (CARC) or a hazardous industrial chemical resistant coating. As used herein, "CARC" means a solvent-based coating (with the solvent being water or an organic liquid) that, when cured, is resistant to degradation by chemical warfare agents, and is easily and effective decontaminated after exposure to such agents. The properties of CARCs are set forth in more detail in MIL-C-29475 (for water-borne CARCs) and MIL-C-46168 (for solvent-borne CARCs), the content of which are incorporated herein by reference. It is believed that the aerosolized resin may be used in combination with any suitable CARC provided that the CARC, whether in uncured or cured form, does not interfere to any material extent with the ion exchange capability of the resin particles. The wetting agent also may comprise a polymeric material. Thorough coating or dusting is necessary for satisfactory results.

Generally, a coating produced by admixing resin particles with a base coating will be preferred over a dust-type coating. The resin particles are not embedded in the coating as well in dust-coatings, so these coatings tend to be more susceptible to abrasion. Dust-coatings also tend to have a less uniform appearance and a grittier texture. It also is more difficult to control the color of dust-coatings. Nevertheless, dust-coating may offer advantages in some circumstances. For example, the grittier texture associated with dust-coating may be preferred for shower floors and the like because it increases slip resistance.

2. COATINGS

The resin of the present invention may be incorporated into a coating that may be applied to nonfluid objects to form a protective film or layer thereon. The coating may be made by suspending the converted resin in a suitable base coating or carrier such that the resin particles are dispersed more or less homogeneously in the carrier. If the converted resin particles are agglomerated as a result of milling or other earlier processing steps, they should be deagglomerated, for example, in an attritter, before being added to the carrier.

The particle size of the converted resin preferably is selected such that the particles are slightly larger (by at least about one micron in diameter), and preferably at least 20 percent larger, than any pigment particles present in the coating. Pigment particles typically are in the range of 3–5 microns, so resin particles sizes in the range of about 4–15 microns (mass median diameter) generally are preferred. This assists in providing access to the surface of the converted resin particles adhered to the coating without causing undue interference with the conventional properties of the applied coating, such as abrasion-resistance. The upper size limitation relates to the size of the nozzle of commercially available paint sprayers rather than a limitation based on effectiveness of the resin particles in devitalizing or deactivating chemical and biological agents, so use of larger particles likely would reduce the efficiency of spray application. Larger particles also may be used, for example, in nonspray coatings.

A narrow particle size distribution also enhances performance of the devitalizing and deactivating agents in coatings. Particles substantially larger than the preferred range are likely to cause surface defects and render the coated surface more susceptible to abrasion. Particles substantially smaller than the preferred range are unlikely to be effective because it is unlikely that any part of their surfaces will be exposed above the level of the coating. An excess of substantially smaller particles also will increase the distance between the exposed particles of the preferred size, such that areas of the surface may be unprotected.

The carrier may be any material that is compatible with the surface to be coated and that does not interfere, whether in cured or uncured form, to any material extent with the ion exchange capability of the converted resin. Preferably, the volume and consistency of the carrier will permit migration of the converted resin particles to the surface of the coating during drying and/or curing. The properties of the carrier may be selected based on performance criteria applicable to a particular substrate, such as flexibility, abrasion resistance and chemical resistance. The carrier may, for example, comprise a paint-type coating such as a water- or solvent borne CARC or hazardous industrial chemical resistant coating or a polymeric material. The carrier also may comprise a coating that is selectively permeable to specific fluids such as polytetrafluoroethylene.

The carrier preferably will comprise pigments and extenders, although it also is possible to use the converted resin particles in combination with a nonpigmented ("clear coat") carrier. As used herein, "extender" means any paint resin system (but not including the converted resin of the present invention), solvents, and other nonpigment coating components. Such carrier systems are thought to offer superior abrasion-resistance than polymeric carriers that are not solvent-borne. Water-based and organic solvents may be used provided that they do not interfere to any material extent with the ion exchange capability of the converted resin. It is believed, for example, that hexane would not be a suitable solvent. The extender also may be a polymeric material, such as a flexible urethane (polyurea), enamel, acrylic, latex, or epoxy.

For pigmented base coatings, the volume of converted resin particles preferably is approximately equal of the volume of pigment particles. This contributes to a uniform distribution of converted resin particles in the coating after is it applied. The pigment particle density preferably is greater than the density of the resin particles.

The quantity of the converted resin admixed with the carrier may vary with the nature of the carrier and the performance characteristics desired in the coating. The quantity of converted resin also may vary with the color of coatings using a common extender system due to changes in the pigments. Generally, the determination of the quantity of converted resin to be admixed with the carrier involves balancing the ion exchange (deactivating and devitalizing) activity against the coating integrity. Preferably, sufficient resin is provided to form a monolayer of resin particles on the surface of the substrate after drying/curing of the coating is completed.

Superior devitalizing and deactivating activity in the applied coating is expected when the converted resin particles are added to a carrier until a near critical pigment volume is obtained. As used herein, "critical pigment volume" means the maximum volume of particles (pigment and converted resin) that can be added to a given quantity of a coating. Near critical pigment volume means a pigment volume in excess of 90% of the critical volume. A resin content approaching critical pigment volume will provide adequate ion exchange while maintaining the integrity of the coating. Most preferably, for pigmented base coatings, $$V_{resin} = V_{pigment} \cong V_{critical}$$

where $V_{resin}$ is the volume of converted resin particles, $V_{pigment}$ is the volume of pigment, and $V_{critical}$ is the critical pigment volume. This quantity and proportion of converted resin particles are likely to result in an optimal amount of converted resin particles distributed substantially uniformly on the surface of the substrate to which the coating is applied. The combined volumes of the pigment particles and the converted resin particles should not exceed the capacity of the binding resin in the coating to maintain the physical integrity of the cured coating with the extended pigment volume.

The resultant admixture may be applied to a surface of the object to be coated by any suitable conventional means, for example, brushing, rolling, spraying, troweling, pouring or the like. The admixture may be applied in multiple coats if necessary, but multiple coats are not thought to either help or hinder performance of the devitalizing or deactivating substance.

Control of environmental conditions, such as cure temperature and relative humidity, during drying of the coating may allow the resin particles to preferentially migrate to the coating surface. Although these condition vary with the binding resin present in the carrier, cure temperatures in the range of about 60° to 90° F. and relative humidities in the range of about 70 to 90 percent generally favor a drying time sufficient to allow migration of the resin particles to the coating surface.

It may be advantageous to apply a primer to the substrate before application of the admixture topcoat to minimize migration of chemicals from the topcoat to the substrate. It also may be advantageous to apply the admixture to a substrate using processes known in the art that provide an electrostatic charge to the substrate surface to provide more uniform coverage and assist in migration of the converted resin particles to the surface of the coating.

Although selection of a coating suitable for inclusion of resin particles generally is preferred, coatings that are not suitable for inclusion of resin particles due to interference from the binding resin or the pigment particles nevertheless may be used, especially when these coating otherwise have particularly preferred physical properties. Such coatings may be treated to allow them to be used in combination with resin particles. For example, the surface of an otherwise unsuitable coating may be mechanically abraded or partially dissolved to expose the resin particles such that their activity against target agents is unimpeded. A fixative layer, such as an adhesive or top coat, also may be applied to the surface of an otherwise unsuitable coating and a layer of resin particles adhered to the fixative layer.

The long-term effectiveness of the devitalizing and deactivating substance in coatings has not yet been studied, although this likely will vary with the conditions to which the coated objects are exposed. It is thought that under ordinary conditions the effective life of the converted resin particles will be at least roughly comparable to the effective life of the overall coating. No field test to monitor coating effectiveness has been developed, although iodine detection tests are available for other applications.

DEVITALIZING/DEACTIVATING

As described above, the converted resin particles may be used to decontaminate nonfluid objects that have been exposed to biological agents. They also may be used to provide a protective coating on nonfluid objects that are likely be exposed to biological agents such that the coating is capable of devitalizing these agents on demand (at least until the devitalizing substance present in the coating has been exhausted) without significant detriment to the object's usual utility and without application of a discrete decontamination or devitalization substance or procedure after exposure to the agent. The protective coating may be applied not only to objects that are likely to be exposed to biological agents on a more or less regular basis, but also to objects that may be exposed to such agents in the event of a catastrophe.

The converted resin particles also may be used to deactivate chemical agents and other industrial toxic chemicals with a $\pi$ bond of sufficient energy to facilitate the reaction with iodine. The chemical agent deactivating particles may be used to decontaminate fluids that may contain chemical agents, to decontaminate nonfluid objects that may have such agents on their surfaces, or to provide a protective coating on nonfluid objects that are likely to be exposed to such agents. The protective coating may provide increased resistance to chemical agents even if it is not capable of deactivating all such possible agents. In certain circumstances, the chemical agent deactivating particles also may be capable of devitalizing biological agents.

The effectiveness of the converted resin particles in accomplishing devitalization and deactivation depends on the ionization potential of the target agent, the distance between the agent and the converted resin ion source, and the existence of a pathway between the agent and the ion source that an halide ion can travel. For example, the pore size of some coatings is thought to be large enough that iodine ions may pass through the pores and an acceptable level of devitalization and/or deactivation may be accomplished even though the resin particles do not directly contact the agent. However, access to the iodine ions associated with the resin particles is critical. If the converted resin particles are completely covered by an adhesive, for example, the effectiveness of devitalization and deactivation are greatly reduced.

Success in devitalizing and deactivating biological and chemical agents depends largely on placing the converted resin in contact with such agents. Superior results are obtain when the converted resin is able to directly contact the agent and remain in contact with the agent for a predetermined time.

The time necessary for the devitalizing and deactivating capability of the resin particles to take effect depends on the closeness of the contact between the particles and the target agent and the type of agent. Devitalization, if it is going to occur, may take place within a few minutes or less for vegetative cells, and within tens of minutes for spores. Deactivation of chemical agents, if it is going to occur, may take place within tens of minutes.

TESTING

The iodide-resin of the present invention has been successfully tested against chemical warfare agents GD and VX, as well as virus and spore forming bacteria.

Triosyn® T40 and T50 activated resins containing 40% and 50% iodine, respectively, in bead or fragment form, were tested against liquid suspensions of various biological agents, including *Bacillus subtilis var. niger* spores ("Bg spores") and *Erwinia herbicola* ("Eh"). A nonactive resin was used as a control. Nonactive resin refers to a nonhalogenated ion exchange resin in the form of beads of about 1.5 mm diameter (i.e., ion exchange resin beads that have not been activated, ground into finely divided particles, or converted as described herein), but that have been washed and otherwise processed through the stages described prior to activation. The type and form of activated resin, exposure time, target organism and percent reduction are shown in Table 1.

TABLE 1

| Resin | Exposure (min) | Organism | Reduction (percent) |
| --- | --- | --- | --- |
| T40 bead | 30 | Eh | 99.9999 |
| T40 bead | 60 | Eh | >99.9999 |
| T40 bead | 120 | Bg spores | 80 |
| T40 bead | 240 | Bg spores | 97 |
| T50 bead | 60 | Bg spores | 95 |
| T50 bead | 120 | Bg spores | 99.7 |
| T50 bead | 240 | Bg spores | 99.99 |
| T50 fragment | 5 | Bg spores | 91 |
| T50 fragment | 30 | Bg spores | 99.9 |
| T50 fragment | 60 | Bg spores | >99.9998 |

Figure 1:
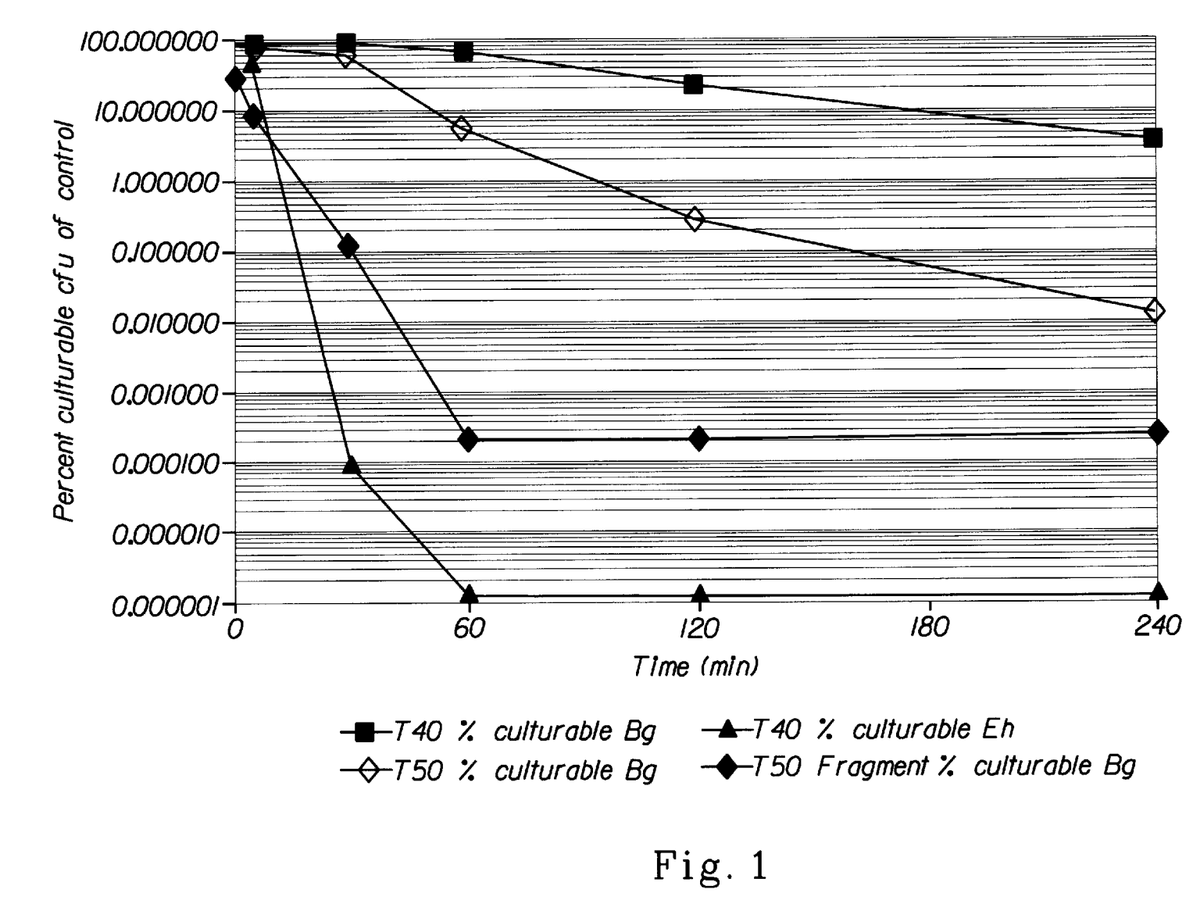
FIG. 1 is a graph showing the effectiveness of an activated (but not converted) resin against liquid suspensions of selected biological agents.

As shown in Table 1, reduction in viability generally was at least 80% effective at the exposure times indicated, with no reduction in viability observed with nonactive resin. The results are shown graphically in FIG. 1.

TABLE 2

| Type of Paint | Average Reduction vs. Control |
| --- | --- |
| Solvent borne urethane (CARC) with additive | >99% vs. *Erwinia herbicola* |
| Water borne urethane (CARC) with additive | 99.4% vs. *Erwinia herbicola* |
| Latex with additive | >99.9% vs. *Erwinia herbicola* |
| Enamel with additive | >99.9% vs. *Erwinia herbicola* |

Table 2 provides reduction values for coating samples prepared with a triiodide-resin according to the present invention. The converted resin was prepared from Triosyn® T-50 resin that had been ground to particles in the range of about 3–15 microns and converted using crystalline of iodine such that the converted resin contained about 50% iodine. The converted resin was added to samples of commercially available coatings. The water borne CARC had 50% resin added based on paint solids and the solvent borne CARC, latex and enamel each had 75% resin added based on paint solids. Non-iodinated samples of the same base coating formulations were used as controls. The coatings were applied to test coupons and allowed to cure.

The test coupons were coated with a liquid suspension of *Erwinia herbicola* (Eh) at $1\times10^6$ colony forming units (CFU) per milliliter. Contact time was 15 minutes. Paint coupons were extracted in phosphate-buffered saline and plated to determine culturable CFUs remaining. The percent reduction values represent the average reduction in culturable CFUs on the test coupons compared to the average CFUs remaining on the appropriate control samples.

A triiodide-resin according to the present invention was tested against the chemical warfare agents GD, HD, and VX. The converted resin was prepared from Triosyn® T-50 resin that had been ground to particles in the range of about 3–15 microns and converted using crystalline of iodine such that the converted resin contained about 50% iodine. 10 g converted resin samples were spiked with 2 microliters of GD, HD and VX, respectively (the "initial quantity" depicted graphically in FIG. 2 for GD and VX). Noniodinated ion exchange resin beads (about 1.5 mm diameter) used as a control also were spiked with 2 microliters of each of these agents.

After an exposure time of one hour, the agents were extracted from the samples using chloroform and analyzed by gas chromatography to give the "recovery quantity," or amount of the unreacted agent remaining in the sample at the end of this time. The quantity of breakdown products resulting from interaction of the agents with the converted resin also was determined for GD and VX.

Figure 2:
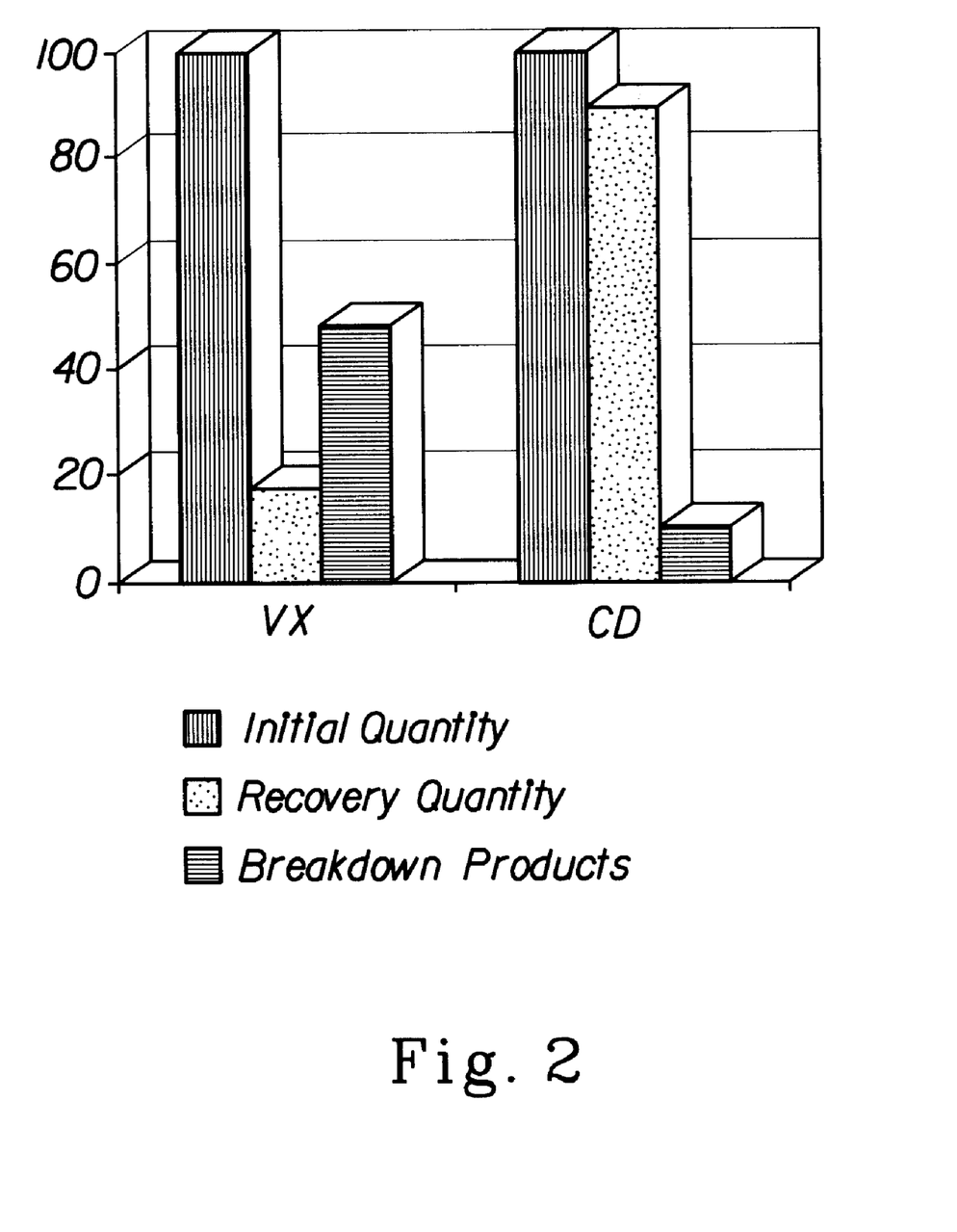
FIG. 2 is a graph showing the effectiveness of a triiodide-resin according to the present invention against the chemical warfare agents VX and GD.

As shown in FIG. 2, a significant reduction in the effective amount of VX was observed. Minimal reduction was observed for GD, although the presence of breakdown products suggests that reduction may be occurring at a slow rate. Based on preliminary data, recovery quantities for HD are expected to be similar to those observed for GD. No measurable reduction was noted for the nonactive resin control samples.

Throughout this specification, when a range of conditions or a group of substances is defined with respect to a particular characteristic (e.g., temperature, pressure, time and the like) of the present invention, the present invention relates to and explicitly incorporates each and every specific member and combination of sub-ranges or sub-groups therein. Any specified range or group is to be understood as a shorthand way of referring to each and every member of a range or group individually as well as each and every possible sub-range and sub-group encompassed therein; and similarly with respect to any sub-ranges or sub-groups therein. Thus, for example, a pressure greater than atmospheric is to be understood as specifically incorporating each and every individual pressure state, as well as sub-range, above atmospheric, such as, for example, 2 psig, 5 psig, 20 psig, 35.5 psig, 5 to 8 psig, 5 to 35, psig 10 to 25 psig, 20 to 40 psig, 35 to 50 psig, 2 to 100 psig, etc.

Although a specific embodiment of the invention has been described herein in detail, it is understood that variations may be made thereto by those skilled in the art without departing from the spirit of the invention or the scope of the appended claims.

What is claimed is:

1. A substance capable of reducing the effectiveness of a halide-reactive target agent, comprising:

halide-resin particles comprising polyhalide ions having a valence of −1 absorbed or impregnated into resin particles and characterized in that an activated halogenated resin is divided into particles substantially in the range of about 0.1–300 microns before exposure to a sufficient amount of a halogen-substance absorbable by the activated resin to form converted resin particles having a greater proportion of available ionic halogen, said halogen-substance being selected from the group consisting of $I_2$, $Br_2$, and polyiodide ions having a valence of −1, said converted resin particles capable of being dispersed as a dry aerosol.

2. A substance according to claim 1, wherein the halide-resin particles are further characterized in that an activated halogenated resin is divided into particles substantially in the range of about 0.1–3 microns before exposure to the halogen-substance.

3. A substance according to claim 1, wherein the halide-resin particles are further characterized in that an activated halogenated resin is divided into particles substantially in the range of about 3–15 microns before exposure to the halogen-substance.

4. A substance according to claim 1, wherein the halide-resin particles are further characterized in that an activated halogenated resin is divided into particles substantially in the range of about 15–300 microns before exposure to the halogen-substance.

5. A coating capable of reducing the effectiveness of a halide-reactive target agent, comprising:
   halide-resin particles comprising polyhalide ions having a valence of −1 absorbed or impregnated into resin particles and characterized in that an activated halogenated resin is divided into particles substantially in the range of about 0.1–300 microns before exposure to a sufficient amount of a halogen-substance absorbable by the activated resin to form converted resin particles having a greater proportion of available ionic halogen, said halogen-substance being selected from the group consisting of $I_2$, $Br_2$, and polyiodide ions having a valence of −1; and
   a carrier holding said converted resin particles in suspension, said suspension suitable for use as a coating.

6. The coating according to claim 5, wherein the halide-resin particles are further characterized in that an activated halogenated resin is divided into particles substantially in the range of about 0.1–3 microns before exposure to the halogen-substance.

7. The coating according to claim 5, wherein the halide-resin particles are further characterized in that an activated halogenated resin is divided into particles substantially in the range of about 3–15 microns before exposure to the halogen-substance.

8. The coating according to claim 5, wherein the halide-resin particles are further characterized in that an activated halogenated resin is divided into particles substantially in the range of about 15–300 microns before exposure to the halogen-substance.

9. The coating according to claim 5, wherein the carrier does not materially interfere with the ion exchange capability of said converted resin.

10. The coating according to claim 5, wherein the carrier includes a predetermined volume of pigment particles and the volume of converted resin particles suspended in said carrier is approximately equal to the volume of pigment particles.

11. The coating according to claim 10, wherein the combined volumes of the pigment particles and the converted resin particles approach the critical pigment volume of the carrier.

12. The coating according to claim 11, wherein the combined volumes of the pigment particles and the converted resin particles are at least about 90% of the critical pigment volume of the carrier.

13. The coating according to claim 5, wherein the carrier includes pigment particles, the combined volume of the pigment particles and the converted resin particles approaching the critical pigment volume of the carrier.

14. The coating according to claim 5, wherein the particles of the converted resin are at least 20 percent larger than the particles of any pigment present in the carrier.

15. The coating according to claim 5, wherein the carrier comprises a chemical warfare agent resistant coating.

16. The coating according to claim 5, wherein the converted resin is capable of reducing the effectiveness of target agents selected from the group consisting of chemical agents, biological agents, and biologically generated toxins.

17. The coating according to claim 5, wherein the carrier comprises a hazardous industrial chemical resistant coating.

18. The coating according to claim 5, wherein the carrier comprises a coating that is selectively permeable to specific fluids.

19. The coating according to claim 5, wherein the carrier comprises a latex.

20. A method of making a protective coating, comprising the steps of:

providing an activated halide-resin;

forming the activated resin into particles;

selecting resin particles substantially in the range of about 0.1–300 microns;

exposing the resin particles to a sufficient amount of a halogen-substance absorbable by the activated resin to form converted resin particles having a greater proportion of available ionic halogen, the halogen-substance being selected from the group consisting of $I_2$, $Br_2$, and polyhalide ions having a valence of −1;

providing a carrier capable of holding said converted resin particles in suspension; and suspending said activated particles in said carrier.

21. The method according to claim 20, wherein the step of selecting resin particles includes the step of:

selecting resin particles substantially in the range of about 0.1–3 microns.

22. The method according to claim 20, wherein the step of selecting resin particles includes the step of:

selecting resin particles substantially in the range of about 3–15 microns.

23. The method according to claim 20, wherein the step of selecting resin particles includes the step of:

selecting resin particles substantially in the range of about 15–300 microns.

24. The method according to claim 20, wherein the step of exposing the resin particles to a sufficient amount of a halogen-substance to form converted resin particles includes the step of:

causing at least a portion of said halogen-substance to be absorbed by the activated resin at elevated temperature and at elevated pressure, said elevated temperature being a temperature higher than 100° C. and up to 210° C., said elevated pressure being a pressure greater than atmospheric pressure and up to 100 psig.

25. The method according to claim 20, wherein the step of providing a carrier includes the step of:

selecting a carrier that does not materially interfere with the ion exchange capability of the converted resin.

26. The method according to claim 20, wherein the step of providing a carrier includes the step of providing a predetermined volume of pigment particles and the step of suspending the converted resin particles in the carrier includes the step of suspending a volume of converted resin particles approximately equal to the volume of pigment particles.

27. The method according to claim 26 further including the step of:

selecting the predetermined volume of the pigment particles and a volume of converted resin particles such that the combined volumes approach the critical pigment volume of the carrier.

28. The method according to claim 27 further including the step of:

selecting the predetermined volume of the pigment particles and a volume of converted resin particles such that the combined volumes are at least about 90% of the critical pigment volume of the carrier.

29. The method according to claim 20, wherein the step of providing a carrier includes the step of providing a carrier including pigment particles and the method further includes the step of:

selecting a volume of pigment particles and a volume of converted resin particles such that the combined volumes approach the critical pigment volume of the carrier.

30. The method according to claim 20, wherein the step of selecting resin particles includes the step of:
selecting resin particles that are at least twenty percent larger than the particles of any pigment present in the carrier.

31. The method according to claim 27, wherein the step of providing a carrier includes the step of providing a carrier having a binding resin and the method further includes the step of:
selecting a volume of the pigment particles and a volume of converted resin particles such that the combined volumes do not exceed the capacity of the binding resin to maintain the physical integrity of the cured coating with the extended pigment volume.

32. The method according to claim 20, further including the step of:
selecting a pigment particle density greater than the density of the resin particles.

33. The method according to claim 20, further including the step of:
selecting environmental conditions for drying the coating, said environmental conditions comprising a combination of cure temperature and relative humidity that yield a drying time sufficient to allow the resin particles to preferentially migrate to the coating surface.

34. The method according to claim 33, wherein the cure temperature is in the range of about 60° to 90° F. and the relative humidity is in the range of about 70 to 90 percent.

35. The method according to claim 20, wherein the carrier interferes with the activity of the resin particles, said method further including the steps of:
applying the coating to a substrate; and
treating the coating to improve the effectiveness of the resin particles.

36. The method according to claim 35, wherein the treating step includes the step of:
mechanically abrading the coating surface to expose the resin particles such that their activity against target agents is unimpeded.

37. The method according to claim 35, wherein the treating step includes the step of:
partially dissolving the coating surface to expose the resin particles such that their activity against target agents is unimpeded.

38. The method according to claim 35, wherein the treating step includes the steps of:
applying a fixative layer to the coating surface; and
adhering a layer of resin particles to the fixative layer.

39. A demand chemical-agent deactivator, comprising:
halide-resin particles having a particle size substantially in the range of about 0.1–300 microns, said halide-resin particles comprising polyhalide ions having a valence of –1 absorbed or impregnated into resin particles.

40. A resin composition, comprising:
halide-resin particles comprising polyhalide ions having a valence of –1 absorbed or impregnated into resin particles having a particle size substantially in the range of about 0.1–15 microns.

41. The resin according to claim 40, wherein said halide-resin is characterized in that an activated halogenated resin is divided into particles substantially in the range of about 0.1–15 microns before exposure to a sufficient amount of a halogen-substance absorbable by the activated resin to form converted resin particles having a greater proportion of available ionic halogen, said halogen-substance being selected from the group consisting of $I_2$, $Br_2$, and polyiodide ions having a valence of –1.

42. A resin composition, comprising:
halide-resin particles comprising polyhalide ions having a valence of –1 absorbed or impregnated into resin particles and characterized in that an activated halogenated resin is divided into particles substantially in the range of about 15–300 microns before exposure to a sufficient amount of a halogen-substance absorbable by the activated resin to form converted resin particles having a greater proportion of available ionic halogen, said halogen-substance being selected from the group consisting of $I_2$, $Br_2$, and polyiodide ions having a valence of –1.

43. A method of making a resin composition, comprising the steps of:
providing an activated halide-resin;
forming the activated resin into particles;
selecting resin particles substantially in the range of about 0.1–300 microns; and
forming converted resin particles having a greater proportion of available ionic halogen.

44. A method of deactivating a halide-reactive target agent, comprising the steps of:
providing an activated halide-resin;
forming the activated resin into particles;
selecting resin particles substantially in the range of about 0.1–300 microns;
exposing the resin particles to a sufficient amount of a halogen-substance absorbable by the activated resin to form converted resin particles having a greater proportion of available ionic halogen, the halogen-substance being selected from the group consisting of $I_2$, $Br_2$, and polyhalide ions having a valence of –1; and
placing said converted resin particles in contact with a target agent selected from the group consisting of chemical agents, biological agents, and biologically generated toxins.

45. The method according to claim 44, wherein the step of placing converted resin particles in contact with a target agent includes the steps of:
providing a carrier capable of holding said converted resin particles in suspension;
suspending said converted particles in said carrier; and
applying the suspension to a surface.

46. The coating according to claim 5, wherein the carrier comprises a urethane.

47. The coating according to claim 5, wherein the converted resin is capable of reducing the effectiveness of a target chemical agent.

48. The coating according to claim 5, wherein the converted resin is capable of reducing the effectiveness of a target biological agent.

49. The coating according to claim 5, wherein the converted resin is capable of reducing the effectiveness of a target biologically generated toxin.

* * * * *